United States Patent [19]

Akamatsu et al.

[11] 4,363,781
[45] Dec. 14, 1982

[54] DISCRETE TYPE AUTOMATED CHEMICAL ANALYTIC APPARATUS

[75] Inventors: Akihiro Akamatsu; Masaki Takeuchi; Kiyoshi Yamashita, all of Otawara, Japan

[73] Assignee: Tokyo Shibaura Denki Kabushiki Kaisha, Japan

[21] Appl. No.: 246,936

[22] Filed: Mar. 24, 1981

[30] Foreign Application Priority Data

Mar. 31, 1980 [JP] Japan .................. 55/41881
Apr. 15, 1980 [JP] Japan .................. 55/49866

[51] Int. Cl.³ ............... G01N 35/04; G01N 35/06; G01N 33/48
[52] U.S. Cl. .................... 422/65; 364/497; 422/66; 422/67; 422/100; 422/102
[58] Field of Search .............. 422/64, 65, 66, 67, 422/100, 103; 141/130; 364/497, 498

[56] References Cited

U.S. PATENT DOCUMENTS

| | | | |
|---|---|---|---|
| 3,481,709 | 12/1969 | Slone | 422/66 |
| 3,551,112 | 12/1970 | Sequeira et al. | 422/65 |
| 3,576,605 | 4/1971 | Drake et al. | 422/65 X |
| 3,687,632 | 8/1972 | Natelson | 422/65 X |
| 3,723,066 | 3/1973 | Moran | 422/66 X |
| 4,260,581 | 4/1981 | Sakurada | 422/65 |
| 4,299,796 | 11/1981 | Hogenesch | 422/65 X |

Primary Examiner—Michael S. Marcus
Attorney, Agent, or Firm—Finnegan, Henderson, Farabow, Garrett & Dunner

[57] ABSTRACT

A discrete type automated chemical analytic apparatus, wherein a carrier member reciprocatable in parallel with a reaction line constituted by those of the reaction tubes linearly arranged on an endless belt which are set on the top run of the endless belt supports two reagent-pipetting nozzles in a vertically movable state. The corresponding reagent containers are disposed on an extension of the reaction line. The nozzles through which the reagent is sucked from the reagent containers pipette the sucked reagent into the corresponding reaction tubes at predetermined points on the reaction line in accordance with the movement of the carrier member. The specimen discharge mechanism includes a nozzle for pipetting a specimen at a prescribed point on the reaction line.

6 Claims, 10 Drawing Figures

DISCRETE TYPE AUTOMATED CHEMICAL ANALYTIC APPARATUS

This invention relates to an automated analytic apparatus, and more particularly to the so-called discrete type automated chemical analytic apparatus which is capable of continuously analyzing a large number of specimens with respect to a plurality of items of examination in a single reaction channel.

Recently, it has assumed greater importance to carry out the analytic procedure of a specimen for diagnosis of a disease and provide required data. Moreover, the number of specimens and their items of examination are progressively increasing. In view of such circumstances, therefore, automation of an analytic procedure has become a problem of urgency in hospitals, laboratories or centers which undertake medical examination work. What is most demanded in this case is an improved automated chemical analytic apparatus which enables a limited personnel and space to furnish analytic diagnostic data closely related to human life without errors.

In this connection, the following points should be taken into consideration:

(1) Analysis of an extremely minute amount of a specimen and reagent should be carried out at low cost.

(2) A large number of specimens should be quickly analyzed and the resultant data should be immediately obtained.

(3) A limited personnel should be enabled to carry out analytic procedures of a larger number of specimens with respect to numerous items of examination.

(4) Accurate and precise data should be furnished in good time.

(5) The subject analytic apparatus should be made sufficiently compact to be installed in a limited space.

With the conventional automated analytic apparatus, noticeable improvements have been made in respect of the above-listed requirements. Particularly, with the first and second items, noteworthy improvements have been accomplished. With the other items, however, improvements attempted to-date can not be regarded as fully satisfactory.

The known discrete type automated chemical analytic apparatus in general use is of the so-called fixed type, wherein the points at which a specimen and reagent are pipetted are fixed, in other words, a distance between a pipetting pump and pipetting point is always defined in accordance with an item of examination. Some semifixed type analytic apparatuses have also been proposed wherein the pipetting point can be slightly shifted, if necessary. Generally speaking, the pipetting point can not be freely varied in a conventional apparatus. In other words, the prior art analytic apparatus is not of the type which enables a given amount of a reagent or specimen to be pipetted at any desired point along a reaction line. Therefore, limitation is imposed on the conventional analytic apparatus in respect of the latitude of application, that is, in the sense that a reaction time should be properly chosen in accordance with individual reagents and specimens. Inevitably, therefore, occasions arise in which an improper reaction has to be undertaken, resulting in a decline in the reliability of obtained data of examination.

Consequently, the examiner has hitherto manually changed a pipetting point or an amount of a liquid to be pipetted in order to obtain more accurate data. Demand has therefore been made to automate these manual procedures.

For reference, the aforementioned analytic apparatus is disclosed in the U.S. Pat. No. 3,432,271. In this connection, the Japanese patent disclosure No. 54-5790 may be cited which has attempted to automate the pipetting of a reagent in order to simplify the control of an automated chemical analytic apparatus. Brief description is now given with reference to FIG. 1 of the arrangement of the chemical analytic apparatus of said Japanese patent disclosure No. 54-5790. This disclosed analytic apparatus comprises:

(a) a serum pipetting mechanism periodically repeating the same action regardless of specimen data;

(b) a nozzle through which a serum sample is supplied as a specimen from the mechanism (a);

(c) a washing tank used to clean the outer wall of the nozzle (b);

(d) a main computer for sending forth an instruction based on specimen data;

(e) a large number of first reagent containers;

(f) a turntable on which the first reagent containers (e) are carried and which is driven upon receipt of an instruction from the main computer (d);

(g) a pipette mechanism for dripping the first reagent;

(h) a nozzle connected to said pipette mechanism (g);

(i) a washing tank used to clean the outer wall of the nozzle (h);

(j) a large number of second reagent containers;

(k) a turntable on which the second reagent containers (j) are carried and which is driven upon receipt of an instruction from the main computer (d);

(l) a pipette mechanism for dripping the second reagent;

(m) a nozzle connected to the pipette mechanism (l); and (n) a washing tank used to clean the outer wall of the nozzle (m).

Description is now given of the operation of an automated chemical analytic apparatus (FIG. 1) set forth in the Japanese patent disclosure No. 54-5790. This chemical analytic apparatus further comprises a specimen feeder (q) carrying a plurality of linearly arranged specimen container (p) each holding, for example, serum. Where one of the specimen containers (p) is brought to a point at which a serum is sucked out of the container (p), then the specimen feeder (q) temporarily ceases to be moved. During the rest of the specimen feeder (q), the aforesaid pipette mechanisms (a, g, l) carry out a prescribed action on a reaction line (s) along which a large number of reaction tubes (r) are set side by side. The serum sucked out of the serum container (p) by the pipette mechanism (a) is diluted with deionized water. The diluted serum is pipetted from the specimen container (p) into the corresponding one of the reaction tubes (r) linearly arranged on the reaction line (s) through the nozzle (b). Where one of the reaction tubes (r) is made to face the nozzle (h) for the first reagent while traveling to the right as viewed in FIG. 1, then the turntable (f) for the first reagent is rotated in the direction of an indicated arrow to an extent corresponding to the previously supplied specimen data. When the rotation is brought to rest, the first reagent held in the reagent container (e) set at a prescribed pipetting point is dripped into the reaction tube (r) by the pipette mechanism (g). Where the reaction tube (r) further travels to the second reagent nozzle (m), then the second reagent is drawn into the reaction tube (r) by the pipette mechanism (l).

The serum solution which was subjected to the above-mentioned reaction procedure has its composition is determined by a spectroscope (t) disposed at the terminal end of the reaction line. The result of the spectroscopic determination is transmitted to the main computer (d) through an interface device (u), and also is visibly printed out at an operation and control section (v).

Application of a turntable in the above-described chemical analytic apparatus of the Japanese patent disclosure No. 54-5790 enables a proper reagent to be automatically selected, eliminating the troublesome work of manually exchanging reagent containers. Further, the analytic apparatus automates the suction and pipetting of a serum and reagent, and enables the uniform operation of a control system and the simplification of its arrangement, thereby assuring a high reliability.

With the aforementioned analytic apparatus, however, the points at which the suction and pipetting of a serum and reagent are carried out are all fixed in place. With the apparatus, therefore, it is impossible to control an interval between the point of time at which pipetting is carried out and that at which a final analysis is performed. For instance, even where a specimen requiring an instant analysis is presented and a reagent reaction relative to the specimen can be finished in a short time, the quick operation of the analytic apparatus of the above-mentioned disclosed patent application is obstructed by the rather lengthy reaction time prescribed in the specification, presenting difficulties in meeting urgent requirements. In other words, the apparatus lacks the freedom to match a reaction time with a specimen to be examined. This means that not only time loss but also an excessively protracted reaction between a serum and reagent results, leading to the production of inaccurate data. Moreover, with the analytic apparatus, turntables occupy a considerably large space, presenting difficulties in rendering the apparatus compact.

It is accordingly the object of this invention to provide a new discrete type automated chemical analytic apparatus which is freed of the above-mentioned difficulties accompanying the conventional automated chemical analytic apparatus, can freely and properly adjust a reaction time in accordance with the kind of a specimen to be medically examined and the items of medical examination, has an increased latitude of application, and is capable of quickly and accurately examining a large number of specimens and also being rendered compact.

With an automated chemical analytic apparatus according to a preferred embodiment intended to attain the above-mentioned object, a plurality of conduit nozzles for the discharge of a reagent are movably supported side by side by a carrier member along a reaction line. Reagent containers are disposed in an extension of the reaction line. A nozzle through which a reagent has been sucked up from the corresponding container is moved by the carrier member to a point facing one of the reaction tubes arranged on the reaction line. At this point, the sucked reagent is pipetted into the reaction tube. A timing in which the reagent is dripped into the reaction tube is properly determined in conformity with a time of reaction between the reagent and a specimen.

With another preferred embodiment, a carrier member supports not only reagent discharge conduit nozzles, but also a suction conduit nozzle through which the reacted solution is conducted to a spectroscopic section from a selected reaction tube on the reaction line. While the carrier member is moved along the reaction line, a reagent is drawn into a selected reaction tube on the reaction line through the corresponding nozzle. The reacted solution is drawn off from the reaction tube through the suction nozzle brought to an optimum position.

With still another preferred embodiment of the invention, reagent discharge nozzles and suction nozzle are supported by separate carrier members, which are made independently movable along the reaction line. Therefore, the nozzles supported by said separate carrier members enable the reagent to be drawn into the reaction tube or sucked therefrom at any desired point on the reaction line.

The aforementioned preferred embodiments have the following advantages:

(1) A point on the reaction line at which a reagent is to be pipetted into a reaction tube or drawn out therefrom can be freely determined, enabling a minimum and optimum reaction time to be chosen, and thereby eliminating the so-called waiting time. Therefore, the subject analytic apparatus can be rendered ready for the urgent examination of a specimen. Or conversely if necessary, it is possible to cause a reaction to be carried out in a longer time than is generally required.

(2) The subject analytic apparatus has a large latitude of application covering numerous items of medical examination, allowing for the predetermination of optimum conditions of medical examination and assuring high precision of analysis.

(3) It is unnecessary for an examiner to manually set the position of a reagent-pipetting nozzle. Namely, the position of the nozzle can be automatically defined by a program. A large number of reaction tubes arranged on a reaction line need not be provided with the corresponding reagent nozzles. Therefore, the arrangement of the reaction tubes can be simplified, and the work efficiency of the examiner is prominently elevated.

(4) With the conventional chemical analytic apparatus, a troublesome work of cleaning the interior of a syringe was involved, each time the items of examination were changed. However, the present invention eliminates such necessity. Namely, any other required reagent has only to be set at a prescribed spot. Consequently, the change of the items of examination and preparatory work for analysis can be finished in such a short time as can be counted in the unit of seconds, as against several minutes consumed in the prior art analytic apparatus.

(5) The reagent does not flow, as in the prior art, from the reagent suction nozzle to the syringe and then to the reagent discharge nozzle. With the present invention, a single nozzle is concurrently used for suction and discharge, preventing the reagent from entering the syringe, and consequently making it unnecessary to clean the interior of the syringe itself. It is possible to avoid the uneconomical practice of wasting a large amount of expensive reagents, each time they are exchanged.

This invention can be more fully understood from the following detailed description when taken in conjunction with the accompanying drawings, in which:

FIG. 1 schematically shows the arrangement of a prior art automated chemical analytic apparatus;

FIG. 2 schematically sets forth the arrangement of a discrete type automated chemical analytic apparatus according to a first embodiment of this invention;

Figure 1:
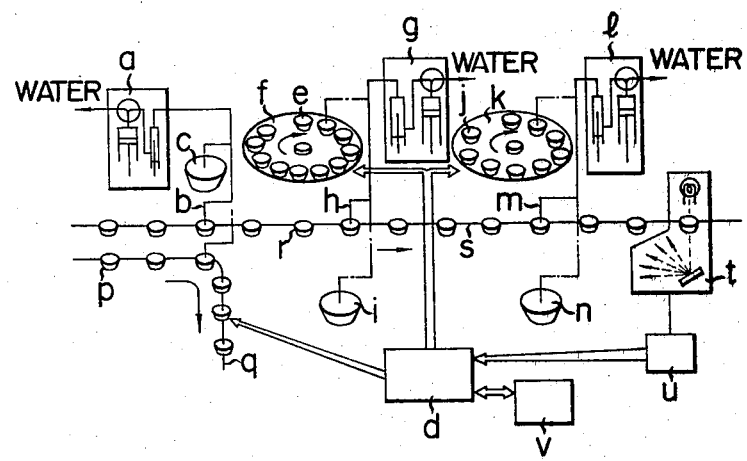
Figure 2:
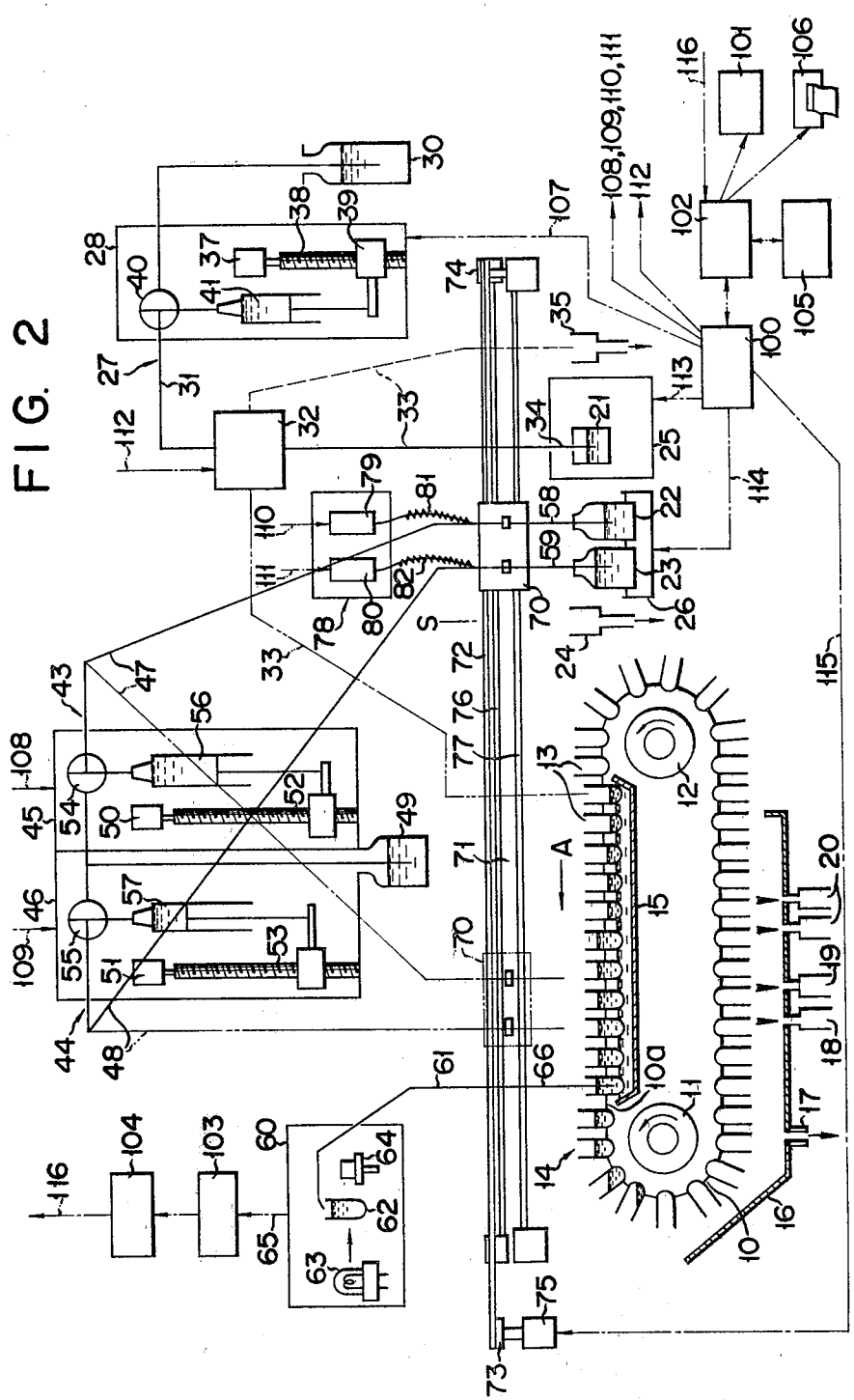
Figures 3, 4:
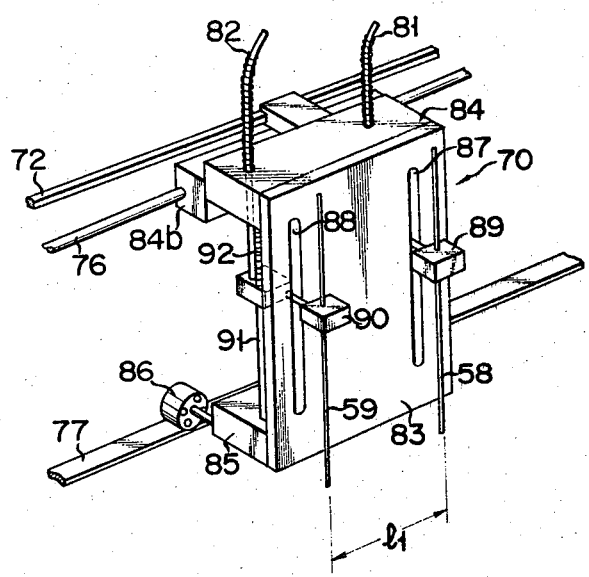
FIG. 3 is an enlarged oblique view of the carrier member of FIG. 2.
FIG. 4 is a lateral view of the same.
Figure 5:
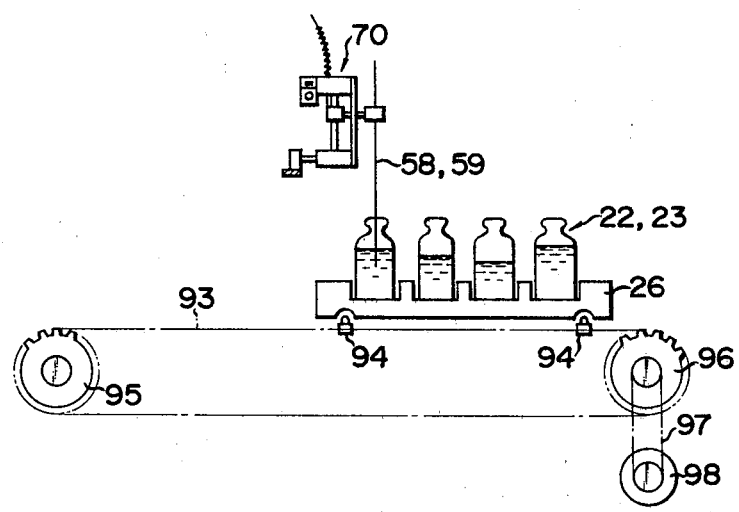
Figure 6:
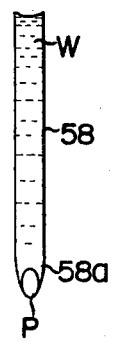
Figure 7:
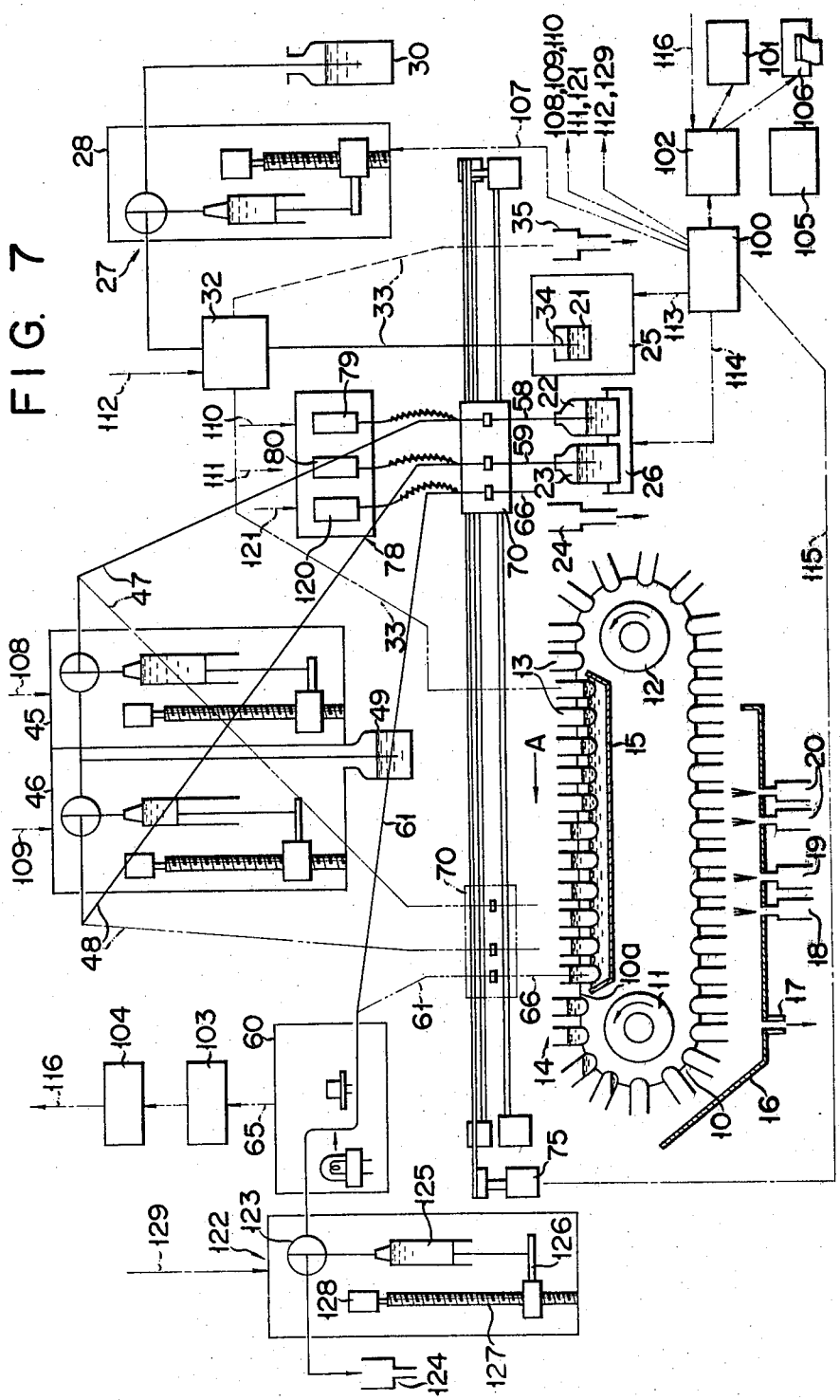
Figure 8:
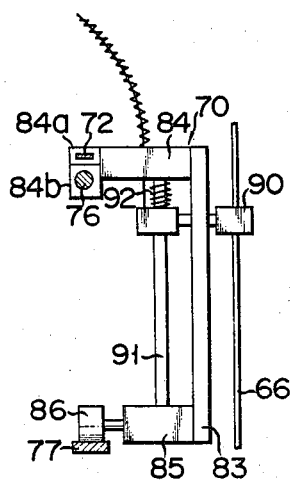
Figure 10:
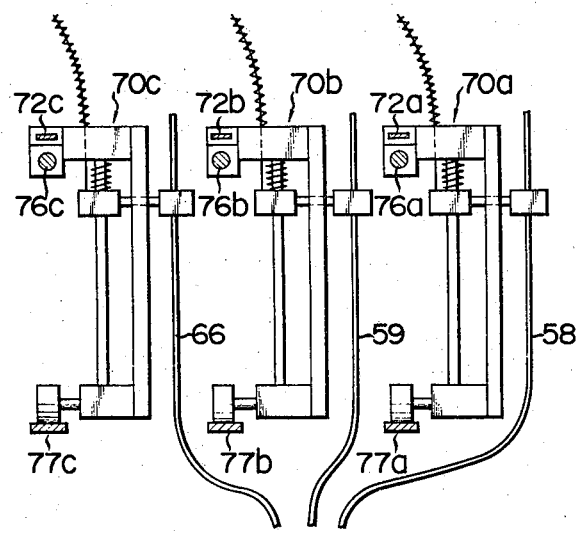
Figure 9:
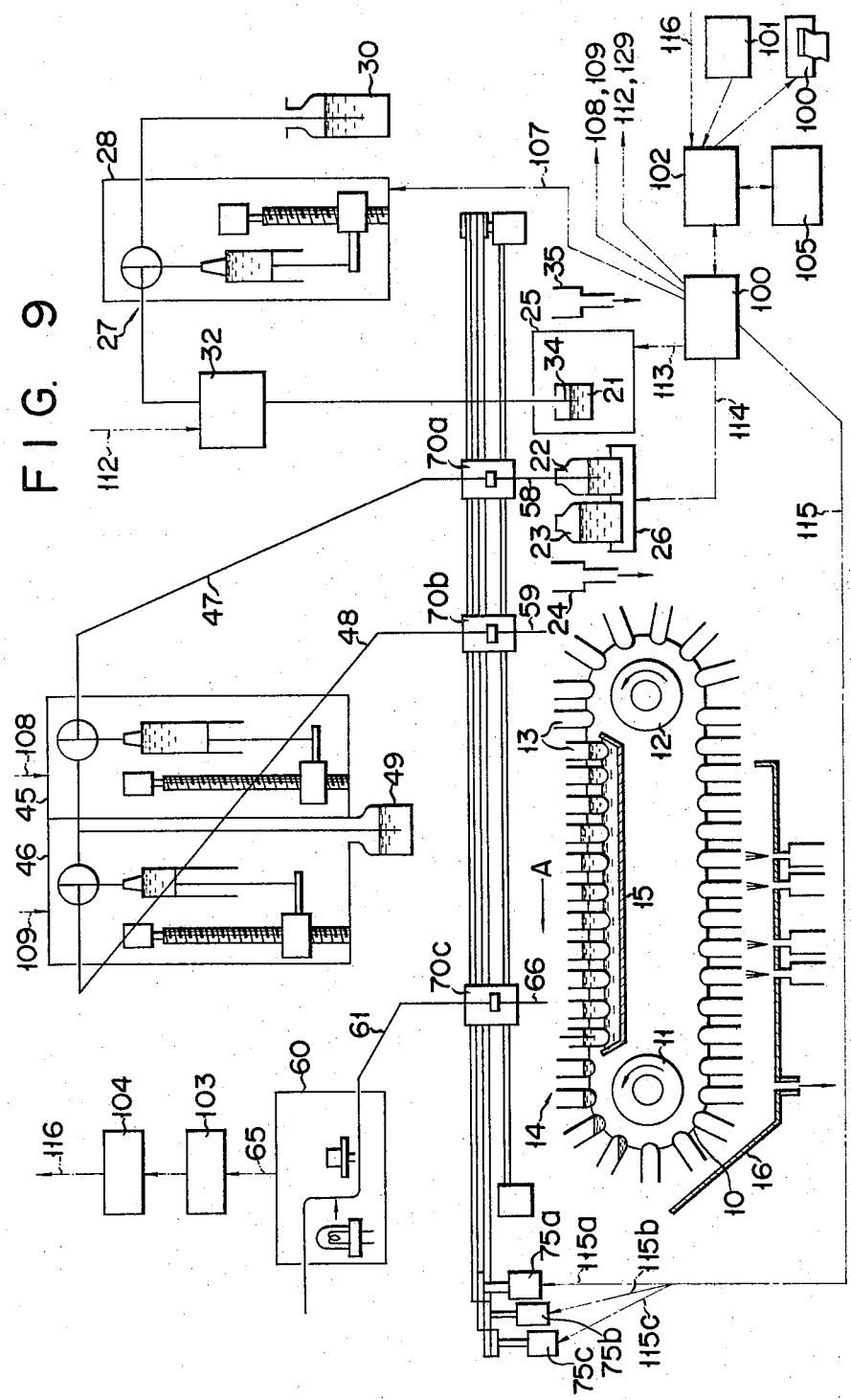

FIG. 5 schematically illustrates a mechanism for driving the reagent cassette of FIG. 2;

FIG. 6 is an enlarged view of the tip of the nozzle used with the analytic apparatus of FIG. 2;

FIG. 7 schematically indicates a discrete type automated chemical analytic apparatus according to a second embodiment of the invention;

FIG. 8 is a lateral view of the carrier member included in the analytic apparatus of FIG. 7 as taken in the same direction as that of FIG. 4;

FIG. 9 schematically shows a discrete type automated chemical analytic apparatus according to a third embodiment of the invention; and FIG. 10 is a lateral view of three carrier members included in the apparatus of FIG. 9 as taken in the same direction as that of FIG. 4.

Description is now given with reference to FIGS. 2 to 6 a discrete type automated chemical analytic apparatus according to a first embodiment of this invention.

Referring to FIG. 2, an endless conveyor belt 10 is driven by a pair of drive shafts 11, 12 rotated in the same direction indicated by the arrows. The top runs 10a of the conveyor belt 10 is intermittently moved in the direction of an arrow A. The total length of the conveyor belt 10 is fitted with a large number of reaction tubes 13 spatially arranged in the direction in which the conveyor belt 10 runs. A group of reaction tubes 13 positioned on the top run 10a defines a sustantially horizontal reaction line 14 for one channel (representing a single reaction line as used in the particular industry). The reaction tubes 13 set on the reaction line 14 are carried while being immersed in a thermostat bath 15. A downward inclined waste receptacle 16 is provided at the rear end of the conveyor belt 10. Said receptacle 16 is fitted with an exhaust port 17, running water-ejecting nozzle 18, deionized water-ejecting nozzle 19 and dry air-jetting nozzles 20 in the order mentioned as counted from the rear end of the conveyor belt 10. When brought to the bottom run side of the conveyor belt 10 these members are used to wash and dry the reaction tubes in order to render them ready for the subsequent application. A specimen container 21, first and second reagent containers 22, 23 and second water receptacle 24 are provided on the right side of the conveyor belt 10 as viewed in FIG. 2 in the order mentioned as counted from the right side. The specimen container 21 is held in a specimen cassette 25. The paired reagent containers 22, 23 are set in a reagent cassette 26. The reagent cassette 26 is moved by the drive mechanism of FIG. 5 crosswise of the reaction line 14 as later described. First and second reagent containers 22, 23 are arranged apparently in the matrix form on the reagent cassette 26, in such a manner that the first and second reagent containers 22, 23 are alternately set in each row. In FIG. 2, a pair of reaction containers 22, 23 are set at prescribed suction points on the reaction line.

A specimen cassette 25 is also made movable crosswise of the reaction line 14 (though not clearly shown in FIG. 2). Specimen containers 21 are arranged crosswise of the reaction line 14. The crosswise movement of the specimen cassette 25 brings a given specimen container 21 to a prescribed specimen-sampling point on the reaction line 14.

With foregoing embodiments of this invention, a serum sampled from an examinee is used as a specimen. In some cases, however, examinee's urine may be applied as a specimen.

A sample discharge device 27 for pipetting a specimen liquid from a selected specimen container 21 to a reaction tube 13 brought to a prescribed point on the reaction line 14 comprises:

a sampling pump 28;

a deionized water bottle 30 connected to the suction side of the sampling pump 28 through a communication pipe (not shown) to supply deionized water to the sampling pump 28;

a pipe 31, one end of which is connected to the discharge side of the sampling pump 28;

a specimen conduit-positioning device 32 connected to the other end of the pipe 31; and a flexible sample conduit 33 whose upper end is connected to the underside of the specimen conduit-positioning device 32 and whose lower free end portion constitutes a nozzle 34 open at the lower end.

The specimen conduit-positioning device 32 (shown in the block form in FIG. 2) may be of the known type, for example, that set forth in the U.S. Pat. No. 3,432,271. The specimen conduit-positioning device 32 pushes the specimen conduit 33 by a swinging motion to a point selected from a suction point (indicated in a solid line in FIG. 2) facing the specimen container 21, a stationary pipetting point (indicated in 2 dots-dash line in FIG. 2) facing a selected reaction tube 13 on the reaction line 14 and a drain point (indicated in a broken line in FIG. 2) facing a waste receptacle 35 set close to the specimen cassette 25. Where the specimen conduit 33 is brought to a suction point, then the conduit positioning device 32 causes the nozzle 34 to move from the normal lifted position for insertion into the specimen container 21. Where the specimen conduit 33 reaches the pipetting point and the drain point, the conduit-positioning device 32 vertically moves the nozzle 34 for the pipetting and discharge of the specimen liquid. The conduit-positioning device 32 receives a sampling nozzle drive signal, as later described, through a signal line 112 to carry out the above-description movement. This specimen-feeding pump assembly 28 comprises a pulse motor 37, lead screw 38 driven by the pulse motor 37, nut member 39 threadedly engaged with the lead screw 38 and syringe 41 whose output terminal is connected to the pipe 31 and deionized water bottle 30 through a 3-way electromagnetic switching valve 40, and whose input side piston rod is connected to the nut member 39. The syringe 41, pipe 31 and conduit 33 are always almost fully filled with deionized water.

Provided above the reaction line 14 are first and second reagent discharge mechanisms 43, 44 for pipetting first and second reagents from the corresponding containers 22, 23 into the selected one of the reaction tubes 13 mounted on the reaction line 14. The reagent discharge mechanisms 43, 44 have substantially the same arrangement as the specimen discharge mechanism 27. The reagent discharge mechanisms 43, 44 respectively comprise pump assemblies 45, 46, flexible pipes 47, 48 connected thereto, and a common deionized water bottle 49 connected to the pump assemblies 45, 46 through pipes. The pump assemblies 45, 46 respectively comprise drive pulse motors 50, 51, nut members 52, 53 threadedly engaged therewith and syringes 56, 57 whose output terminals are connected to flexible pipes 47, 48 through 3-way electromagnetic switching valves 54, 55 and whose input terminal piston rods are connected to the corresponding nut members.

The free end portions of the flexible pipes 47, 48 constitute nozzles 58, 59. As in the specimen-feeding pump assembly 28, the syringes 56, 57 and flexible pipes 47, 48 of the first and second reagent discharge pumps 45, 46 are always almost fully filled with deionized water.

A spectroscopic unit 60 of the known type is provided above the terminal end portion of the reaction line 14. A reacted solution drawn out of the reaction tube 13 through a suction pipe or conduit 61 is brought into a flow cell 62. A light source 63 and detector 64 cooperate to make a spectroscopic measurement of said reacted solution taken into the flow cell 62. A signal indicative of the result of measuring the light absorptivity of the reacted solution is transmitted to a signal line 65. The suction pipe 61 is fitted with a known suction pump (not shown). The lower end portion of the suction pipe 61 acts as a suction nozzle 66. The suction nozzle 66 made to face the terminal end of the reaction line 14 is brought down, when required, to suck up a reacted solution from the reaction tube 13 brought to the terminal end of the reaction line 14. FIG. 2 shows the suction nozzle 66 brought down to a sucking state. The vertical movement of the suction nozzle 66 is effected by proper means, for example, a solenoid.

The first and second reagent nozzles 58, 59 are vertically and spatially supported by a carrier member 70. This carrier member 70 is made movable along a horizontal path 71 positioned above the reaction line 14 and extension thereof in substantially parallel relationship therewith. The two nozzles 58, 59 also move with the carrier member 70.

The reciprocation of the carrier member 70 through the path 71 is effected by the cooperation of a timing belt or string 72 fixed to the carrier member 70, a pair of right and left pulleys 74, 73 for stretching the belt 72 along the path 71 and drive pulse motor 75 connected to the left pulley 73.

Upper and lower parallel elongated guide bars 76, 77 horizontally extend along the path 71 to guide the carrier member 70 exactly along the path 71. The right and left ends of both bars 76, 77 are securely supported by proper means.

The two nozzles 58, 59 supported by the carrier member 70 are normally set in a most retracted, namely, most lifted position, and, when required, are let to move vertically from the position into the corresponding specimen container 21 and first and second reagent containers 22, 23 to suck up the contents thereof. The vertical movement of the two nozzles 58, 59 is effected by a solenoid mechanism 78 schematically set forth in FIG. 2.

The solenoids 79, 80 of the solenoid mechanism 78 are respectively connected to the corresponding nozzles 58, 59 by means of flexible drive wires 81, 82. The solenoids 79, 80 are so arranged as to be retracted when energized and brought down when deenergized.

Description is now given with reference to FIGS. 3 and 4 of the carrier member 70 and associated members. The carrier member 70 comprises a vertical wall plate 83, upper laterally projecting block 84 fixed to the front or back side of the upper portion of the vertical wall plate 83 and lower block 85 fixed to the front or back side of the lower portion of said vertical wall plate 83 in a state laterally projecting in parallel with the upper block 84. The free end edge of the upper block 84 has a stepped portion, on which blocks 84a, 84b are integrally formed. The block 84a is fitted with a timing belt 72. A little below the timing belt 72, a slidable round upper guide bar 76 penetrates the block 84b. The free edge portion of the lower block 85 is fitted with a guide roller 86. This guide roller 86 is made to roll over the surface of a flat lower guide bar 77. A pair of guide rollers 86 are actually provided, though not shown in FIGS. 3 and 4.

Two vertically elongated guide slots 87, 88 are spatially formed in the vertical wall plate 83. The respective slots 87, 88 are fitted with support elements 89, 90. Each of these support elements 89, 90 is enlarged into a block form at both ends, and made movable only vertically. Those of the block portions of the support elements 89, 90 which project outward from the front side of the vertical wall plate 83 are respectively penetrated by the first reagent nozzle 58 and second reagent nozzle 59. In FIGS. 3 and 4 the upper portions of the nozzles are omitted.

A distance $l_1$ between the first and second reagent nozzles 58, 59 is particularly chosen to be substantially equal to a distance between the centers of the first and second reagent containers 22, 23.

As best shown in FIG. 4, the upper and lower blocks 84, 85 are bridged by two vertical guide rods 91, which respectively correspond to the vertical guide slots 87, 88. Those of the block portions of the support elements 89, 90 penetrating the vertical guide slots 87, 88 which are positioned on the backside of the vertical wall plate 83 are made to slide along the corresponding guide rods 91. A compression spring 92 surrounds that section of the guide rod 91 of each of the support elements 89, 90 which is defined between the underside of the upper block 84 and the upper surface of the inner block portion of each support element. The compression spring 92 always urges downward the support elements 89, 90 or nozzles 58, 59. However, the nozzles 58, 59 can be electromagnetically retracted or lifted by means of drive wires 81, 82 against the urging force of the compression spring 92. Where either of the solenoids 79, 80 is deenergized, then the corresponding one of the nozzles 58, 59 is brought down by the urging force of the compression spring 92.

The fact that the nozzle is normally electromagnetically retracted or lifted and, where necessary, is elastically brought down by the action of the compression spring 92 offers the advantage that should the lower end of the elastically movable nozzle be pressed against any obstruction, then the end is brought to rest there and prevented from being further let to move and consequently can be saved from damage or breakage.

The flexible pipes or conduits 47, 48 connectable to the nozzles 58, 59 within the range in which the carrier member 70 travels and the drive wires 81, 82 corresponding the nozzles 58, 59 should actually be made sufficiently long to facilitate the movement of the carrier member 70. In FIG. 2, however, the flexible pipes and wires are schematically illustrated regardless of the above-mentioned requirement.

Referring to the relationship between FIGS. 2 and 3, the pulleys 73, 74 of the timing belt 72 are shown in a state rotated through an angle of 90° in order to better show the pulse motor 75. However, it is to be understood that the pulleys 73, 74 and pulse motor 75 are rotated along a plane parallel with the surface of FIG. 2.

As shown in FIG. 5, first and second reagent containers 22, 23 are arranged on the reagent cassette 26 in the apparently matrix form (four columns shown in FIG. 5) with the first and second reagent containers 22, 23 alternately set in each row. The reagent cassette 26 can be moved along by engagement between cavities formed on the underside of the cassette 26 and upright projections 94 provided on the endless chain belt 93. This belt 93 is stretched across a pair of right and left sprocket wheels 96, 95. The right sprocket wheel 96 is connected to a drive motor 98 by means of a belt 97. Upon receipt of the later described cassette drive signal, the motor 98 is intermittently driven, causing the chain belt 93 to be moved crosswise of the reaction line 14. As a result, first and second reagent containers 22, 23 arranged side by side crosswise of the reaction line 14 are brought to suction points corresponding to the nozzles 58, 59 set above the carrier member 70. The reagent cassette 26, chain belt 93 and motor 98 jointly constitute a device for moving the first and second reagent containers 22, 23.

Description is now given with reference to FIG. 2 of an assembly of electronic circuit blocks 100 to 116 for automatically controlling the operations of the respective constituent mechanisms of a discrete type automated chemical analytic apparatus embodying this invention. The assembly comprises a control circuit 100 for sending forth various control signals; an operation panel 101; an interface device 102 connected between the operation panel 101 and control circuit 100; a log converter 103 for converting signals sent forth from the spectroscopic unit 60 which denote the results of analyzing a specimen into signals instructing further processing; an A-D converter 104 for converting an output signal from the log converter 103 into a digital signal and supplying the digital signal to the interface device 102; a central processing unit (CPU) 105 designed to control the operation of the interface device 102 and store data on the analysis of a specimen; and a printer 106 for printing out required information upon receipt of data on the analysis of the specimen.

A signal instructing the drive of a specimen-feeding pump is supplied from the control circuit 100 to the specimen-feeding pump assembly 28. Signals are issued from the control circuit 100 to the first and second reagent-feeding pumps 45, 46 for their drive through the corresponding signal lines 108, 109. Signals are sent forth from the control circuit 100 to the solenoid mechanism 78 through the signal lines 110, 111 to drive the solenoids. A specimen nozzle drive signal is delivered to the specimen conduit-positioning device 32 through a signal line 112. A specimen cassette drive signal and specimen data signal are supplied from the control circuit 100 to the specimen cassette 25 through a signal line 113. A reagent cassette-driving signal is delivered from the control circuit 100 to the reagent cassette 26 and its drive motor 28 through the signal line 114. A signal is also issued from the control circuit 100 to the pulse motor 75 for its drive through the signal line 115 in order to effect the movement of the carrier member 67. The A-D converter 104 and interface device 102 are connected together by the signal line 116.

Description is now given of the operation of an automated chemical analytic apparatus embodying this invention. The direction of the arrow A of FIG. 2 in which the reaction line 14 travels denotes that in which a reaction time passes (hereinafter referred to as "a time axis direction"). A container 21 holding a plurality of specimens is placed in the specimen cassette 25. The first and second reagent containers 22, 23 are received in the reagent cassette 26. At this time, the carrier member 70 is set at a starting position S facing the waste receptacle 24 acting as a drain.

The examiner operates a keyboard mounted on the operation panel 101. Upon receipt of a signal from the keyboard, the required one of the specimen containers 21 held in the specimen cassette 25 and the required ones of the first and second reagent containers 22, 23 held in the reagent cassette 26 are brought to a point at which the specimen and reagent are to be sucked up into the corresponding nozzles. At this time, the control circuit 100 sends forth signals denoting data on a specimen to be examined, items of examination and a length of time in which analysis should be finished.

Thereafter, the following procedures are automatically carried out in accordance with a preset program. First, deionized water is filled in the nozzles 58, 59 disposed above the carrier member 70 waiting for actuation at the starting position S. At this time a sampling pump 28 is also put into operation. Referring to the first reagent pump 45, the pulse motor 50 is driven upon receipt of a drive signal. The syringe 56 starts sucking by means of the lead screw 52 and nut member. The electromagnetic valve 54 is actuated to take in deionized water. Where the electromagnetic valve 54 is actuated in the opposite direction to cause the syringe 56 to carry out further suction, then deionized water W is filled in the nozzle 58 and an air bubble P is formed at the lower end 58a of the nozzle 58 as shown in enlargement in FIG. 6. The air bubble acts to separate the deionized water from a specimen or reagent. The above-mentioned operation also takes place in the other pumps 28, 46.

Later, the control circuit 100 sends forth a sampling nozzle drive signal through a signal line 112 to actuate the specimen conduit-positioning device 32. At this time, the sampling nozzle 34 is brought down at the suction point to be inserted into the specimen container 21. During this step, the sampling pump 28 is actuated to cause a prescribed amount of specimen liquid to be sucked up into the sampling nozzle 34. Later, the sampling nozzle 34 is lifted to the normal position. The specimen conduit-positioning device 32 begins to swing, causing the sampling nozzle 34 to be brought to a point facing a selected reaction tube 13 set at a prescribed point on the reaction line 14. As a result, a predetermined amount of a specimen liquid is pipetted into the reaction tube 13. Where the specimen conduit-positioning device 32 further swings, then a specimen liquid left in the sampling nozzle 34 is drawn off into the waste receptacle 35 disposed on an extension of the reaction line 14. The discharge of the residual specimen liquid is effected by the pushing action of the deionized water held in the sampling nozzle 34. This pushing action of the deionized water has the effect of cleaning the inner wall of the end portion of the sampling nozzle 34.

Thereafter, the carrier member 70 is slightly moved in the direction in which reaction proceeds, causing both nozzles 58, 59 to exactly face the first and second reagent containers 22, 23. Later when the solenoid 77 is deenergized, both nozzles 58, 59 are brought down to suck up the first and second reagents as shown in FIG. 2. After suction is brought to an end, both nozzles 58, 59 are lifted. Since a distance $l_1$ between both nozzles 58, 59 is made equal to that between the centers of the first and second reagent containers 22, 23, the simultaneous suction of the first and second reagents can be effected, thereby reducing a time to suck up a specimen liquid and reagent (hereinafter simply referred to as a "suction time").

The carrier member 70 travels through the path 71 in the time axis direction, and is brought to rest at a point facing the selected one of the reaction tubes 13. The first reagent is pipetted into the reaction tube 13 through the first reagent nozzle 58.

Whre the carrier member 70 is further moved in the time axis direction, then the second reagent is pipetted into the reaction tube 13 through the second reagent nozzle 59 at another desired point on the reaction line 14. This arrangement is specified for the case where the second reagent quickly reacts.

Where the pipetting of the first and second reagents is brought to an end, then the carrier member 70 is brought back to the original position S by the backward drive of the pulse motor 75. At this time, the first reagent nozzle 58 is brought down into the waste receptacle 24 to cause the liquid left in the reagent nozzle 58 to be discharged. Thereafter, the carrier member 70 is slightly moved to the right as viewed in FIG. 2 to cause the second reagent nozzle 59 to face the waste receptacle 24, thereby releasing the reagent left in the second reagent nozzle 59. The release of the residual second reagent from the second reagent nozzle is effected by the forceful introduction of deionized water into said nozzle as in the case where the residual specimen liquid is discharged. Therefore, the inner wall of the second reagent nozzle is automatically washed by deionized water.

If arrangement is made to let deionized water be always ejected from the second waste receptacle 24, then the outer wall of the nozzle can be washed by the deionized water when the residual liquid is discharged from the nozzle. It may be advised, however, to provide a separate washing device aside the waste receptacle 24. This arrangement is also applicable to the receptacle 35 provided for the specimen nozzle 34.

Where the carrier member 70 is quickly brought to a required point on the reaction line 14 by the selective drive of the pulse motor 75, then the reagent can be easily pipetted into a desired reaction tube 13, thereby making it possible to freely chose a reaction time.

The reagent is carried along the reaction line 14 in a state only sucked into the nozzle portion of the reagent conduit. Therefore, the exchange of a reagent can be easily conducted simply by discharging extremely small residues of the used reagent, thereby assuring the saving of the reagent. This advantage is also assured with respect to the specimen.

Control of a timing in which a specimen liquid and reagents are pipetted from the corresponding nozzles as well as of a distance through which a carrier member is to be moved can be easily undertaken by those skilled in the art by providing a proper program for each of the control circuits.

Description is now given with reference to FIGS. 7 and 8 of a discrete type automated analytic apparatus according to a second embodiment of this invention. The parts the same as those of the first embodiment are denoted by the same reference numerals, description thereof being omitted.

The second embodiment differs from the first embodiment in that the vertically movable suction nozzle 66 is supported on the carrier member 70 on the same line as the first and second reagent nozzles 58, 59 apart therefrom; a solenoid 120 for vertically moving the suction nozzle 66 is additionally provided for the solenoid mechanism 78; and a drive signal line 121 is connected to the control circuit 100. The solenoid 120 is actuated in the same manner as the other solenoids 79, 80.

The suction conduit 61 whose lower end portion constitutes the suction nozzle 66 extends through the spectroscopic section 60 to be connected to a 3-way electromagnetic valve 123 of a suction drive pump 122. The electromagnetic valve 123 is connected to a drain 24 through a conduit and also to a syringe 125. The piston of the syringe 125 is connected to a nut member 126 actuated by a lead screw 127. This lead screw 127 is driven by a pulse motor 128. This pulse motor 128 is driven by a suction pump drive signal supplied from the control circuit 100 through a signal line 129.

The above-mentioned arrangement enables the position of the suction nozzle 66 to be freely charged along the reaction line 14 in accordance with the movement of the carrier member 70, thereby shortening the reaction time. Therefore, the second embodiment can be rendered more adapted for the urgent examination of a specimen.

The carrier member 70 of FIG. 8 has the same side elevation of that of the first embodiment of FIG. 4. The second embodiment differs from the first embodiment only in that the carrier member 70 is provided with three nozzles 58, 59, 66 as against the two nozzles 58, 59 of the carrier member 70 of the first embodiment.

Description is now given with reference to FIGS. 9 and 10 of a discrete type automated chemical analytic apparatus according to a third embodiment of this invention modified from the first and second embodiments. The parts of the third embodiment the same as those of the preceding embodiments are denoted by the same reference numerals, description thereof being omitted. The third embodiment is different from the preceding embodiments in that three carrier members 70a, 70b, 70c are respectively provided for the first reagent nozzle 58, second reagent nozzle 59 and suction nozzle 66, in other words, the respective nozzles 58, 59, 66 are mounted on the corresponding carrier members 70a, 70b, 70c to be driven separately.

The three carrier members 70a, 70b, 70c of the second embodiment are provided, as seen from FIG. 10, with separately driven timing belts 72a, 72b, 72c, upper guide bars 76a, 76b, 76c and lower guide bars 77a, 77b, 77c. The three carrier members 70a, 70b, 70c are spatially arranged in parallel with the reaction line 14. The timing belts 72a, 72b, 72c corresponding to the carrier members 70a, 70b, 70c are driven by the individual drive motors 75a, 75b, 75c (FIG. 8) by means of the corresponding pulleys. These drive motors 75a, 75b, 75c are connected to the control circuit 100 through lines 115a, 115b, 115c branched from a main line 115.

Those skilled in the art can easily design a program for the control circuits to move the three carrier members 70a, 70b, 70c independently by selectively controlling the drive of the three pulse motors 75a, 75b, 75c. It will be noted that nozzle-driving solenoid mechanisms are omitted from FIG. 9 for the sake of the description.

The left end of the suction conduit 66 is actually connected to the same type of suction pump as used in the second embodiment. Said suction pump, however, is omitted from the drawing.

With the third embodiment, the carrier members 70a, 70b, 70c are spatially arranged, as shown in FIG. 10, laterally of the analytic apparatus. Therefore, the lower portions of the nozzles 58, 59, 66 are bent along the reaction line 14 convergently to approach each other as much as possible.

The description of the foregoing embodiments refer to the case where a single line constituted the so-called single channel. Obviously, it is possible to manufacture the so-called multichannel automated chemical analytic apparatus by arranging a plurality of such channels in parallel.

The above-mentioned embodiments relate to the case where two kinds of reagent were pipetted. However, the number of reagents need not to limited to two. The present invention allow for the application of a single reagent or the simultaneous pipetting of three or more reagents.

What we claim is:

1. A discrete type automated chemical analytic apparatus for continuously analyzing a large number of specimens with respect to a plurality of items of examination in a single reaction channel comprising:

endless conveyor means having a top run;

drive means for moving the conveyor means;

a plurality of reaction tubes spatially mounted on the conveyor means in a direction in which said conveyor means is driven, those of said reaction tubes which are set on the top run of the conveyor means jointly defining a reaction line, the direction in which the reaction line travels being a time axis direction;

specimen-holding means;

reagent-holding means;

specimen discharge means for pipetting the specimen into a selected reaction tube on the reaction line from the specimen-holding means, said specimen discharge means including conduit means;

specimen conduit-positioning means for selectively moving the specimen discharge conduit means between a point facing the specimen-holding means at which the specimen is to be sucked and a fixed pipetting point at which the sucked specimen is to be dripped into the selected reaction tube on the reaction line;

reagent discharge means for pipetting a reagent into the selected reaction tube on the reaction line from the reagent-holding means, said reagent discharge means including conduit means;

measuring means providing at the terminal end of the reaction line for the analysis of said reacted specimen, said measuring means including intake conduit means adapted to remove said reacted specimen from said reaction tubes;

means for washing and drying the reaction tubes after removal of said specimen in order to render them ready for a subsequent application;

carrier means for supporting and moving the conduit means of the reagent discharge means from a point facing the reagent holding means to a point facing the selected reaction tube on the reaction line in the time axis direction;

carrier-driving means for reciprocating the carrier means along a path extending substantially in parallel with the reaction line; and a driving mechanism for selectively moving the reagent-holding means crosswise of the reaction line, whereby the reaction time can be adjusted freely and properly in accordance with the kind of specimen and the items of examination.

2. The apparatus according to claim 1, wherein the conduit means of the reagent discharge means include at least two nozzles; and the carrier means is formed of a single carrier member for supporting said at least two nozzles in a spatially disposed and vertically movable state.

3. The apparatus according to claim 1, wherein the reagent-holding means holds various kinds of reagent and are formed of reagent bottles which are arranged in at least two columns in the lengthwise direction of the analytic apparatus and in a large number of rows in the crosswise direction of said apparatus; and the driving mechanism comprises a cassette on which the reagent bottles are to be mounted, drive endless belt engaged with the cassette and disposed crosswise of the reaction line, and pulse motor for intermittently moving the endless belt.

4. The apparatus according to claim 1, wherein the intake conduit means of the measuring means is supported by the carrier means to be moved to a point facing a selected reaction tube on the reaction line.

5. The apparatus according to claim 4, wherein the conduit means of the reagent discharge means includes at least two nozzles; the intake conduit means of the measuring means includes one nozzle; and the carrier means comprises at least two nozzles of the conduit means and a single carrier member for supporting the nozzles of the intake conduit means is a spatially disposed and vertically movable state.

6. The apparatus according to claim 4, wherein the conduit means of the reagent discharge means includes at least two nozzles; the intake conduit means of the measuring means includes one nozzle; the carrier means is formed of at least two carrier members for supporting at least two nozzles of the conduit means separately and in a vertically movable state and another carrier member for supporting the nozzle of the intake conduit means is a vertically movable state; and said carrier members are made independently movable along a path extending substantially in parallel with the reaction line.

* * * * *